(12) United States Patent
Ni et al.

(10) Patent No.: US 11,162,124 B2
(45) Date of Patent: Nov. 2, 2021

(54) ALCOHOL DEHYDROGENASE MUTANT AND APPLICATION THEREOF IN COFACTOR REGENERATION

(71) Applicant: Jiangnan University, Wuxi (CN)

(72) Inventors: Ye Ni, Wuxi (CN); Cheng Zhu, Wuxi (CN); Guochao Xu, Wuxi (CN); Jieyu Zhou, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/847,959

(22) Filed: Apr. 14, 2020

(65) Prior Publication Data

US 2020/0362375 A1    Nov. 19, 2020

Related U.S. Application Data

(63) Continuation of application No. PCT/CN2018/118368, filed on Nov. 30, 2018.

(30) Foreign Application Priority Data

Oct. 30, 2018 (CN) .......................... 201811277370.4

(51) Int. Cl.
 C12N 9/04    (2006.01)
 C12P 13/22   (2006.01)

(52) U.S. Cl.
 CPC ..... *C12P 13/222* (2013.01); *C12Y 101/01001* (2013.01)

(58) Field of Classification Search
 None
 See application file for complete search history.

(56) References Cited

PUBLICATIONS

Zhou et al., J. Am. Chem. Soc. 140:12645-12654, Sep. 2018 (Year: 2018).*
Singh et al., Curr. Protein Pept. Sci. 18:1-11,2017 (Year: 2017).*
Zhang et al., Structure 26:1474-1485, 2018 (Year: 2018).*
GenBank Database Accession No. KAG0660321, Jan. 2021, 1 page (Year: 2021).*
GenBank Database Accession No. EEU06136, Aug. 2009, 2 pages (Year: 2009).*
Xu et al., ACS Sustainable Chem. Eng. 7:15706-15714, 2019 (Year: 2019).*
Airaksinen et al., Nucleic Acids Res. 26:576-581, 1998 (Year: 1998).*
Schultz et al., Proteins Structure and Function, pp. 521-528, Plenum Press, New York, 1987 (Year: 1987).*
Xu et al., ACS Catal. 8:836-8345, Aug. 2018 (Year: 2018).*

\* cited by examiner

*Primary Examiner* — David Steadman
(74) *Attorney, Agent, or Firm* — IPro, PLLC; Na Xu

(57) ABSTRACT

Disclosed is an alcohol dehydrogenase mutant and application thereof in cofactor regeneration, and belongs to the technical fields of enzyme engineering and bioengineering. The alcohol dehydrogenase mutant is obtained by mutating valine at position 84 and/or tyrosine at position 127 in alcohol dehydrogenase having an original amino acid sequence as set forth in SEQ ID No. 1. The alcohol dehydrogenase mutant has high activity for a variety of alcohol co-substrates, and can catalyze these enzyme co-substrates for the regeneration of cofactor NADPH. Compared with the wild-type alcohol dehydrogenase KpADH, the alcohol dehydrogenase mutant has higher activity and catalytic efficiency, and for co-substrate 1,4-butanediol, its $k_{cat}$ value can be up to 75.9 $min^{-1}$, its $k_{cat}/K_m$ value can be up to 2009 $min^{-1} \cdot M^{-1}$, and its $K_m$ value can be as low as 11.3 mM. Therefore, the alcohol dehydrogenase mutant has a higher value in industrial application.

9 Claims, 3 Drawing Sheets

Specification includes a Sequence Listing.

SEQUENCE LISTING

<160> NUMBER OF SEQ ID NOS: 14

<210> SEQ ID NO 1
<211> LENGTH: 342
<212> TYPE: PRT
<213> ORGANISM: Artificial Sequence
<220> FEATURE:
<223> OTHER INFORMATION: Protein translated from synthetic DNA

<400> SEQUENCE: 1

Met Ser Val Leu Ile Ser Gly Ala Ser Gly Tyr Ile Ala Lys His Ile
1               5                   10                  15

Val Arg Val Leu Leu Glu Gln Asn Tyr Lys Val Ile Gly Thr Val Arg
            20                  25                  30

Ser Gln Asp Lys Ala Asp Lys Leu Leu Lys Gln Tyr Asn Asn Pro Asn
        35                  40                  45

Leu Ser Tyr Glu Ile Val Pro Glu Ile Ala Asn Leu Asp Ala Phe Asp
                50                  55                  60

Asp Ile Phe Lys Lys His Gly Lys Glu Ile Lys Tyr Val Ile His Ala
 65                  70                  75                  80

Ala Ser Pro Val Asn Phe Gly Ala Lys Asp Leu Glu Lys Asp Leu Val
                85                  90                  95

Ile Pro Ala Ile Asn Gly Thr Lys Asn Met Phe Glu Ala Ile Lys Lys
                100                 105                 110

Tyr Ala Pro Asp Thr Val Glu Arg Val Val Met Thr Ala Ser Tyr Ala
                115                 120                 125

Ser Ile Met Thr Pro His Arg Gln Asn Asp Pro Thr Leu Thr Leu Asp
            130                 135                 140

Glu Glu Thr Trp Asn Pro Val Thr Glu Glu Asn Ala Tyr Glu Asn Val
145                 150                 155                 160

Phe Thr Ala Tyr Cys Ala Ser Lys Thr Phe Ala Glu Lys Glu Ala Trp
                165                 170                 175

Lys Phe Val Lys Glu Asn Ser Asp Ala Val Lys Phe Lys Leu Thr Thr
                180                 185                 190

Ile His Pro Ser Phe Val Phe Gly Pro Gln Asn Phe Asp Glu Asp Val
            195                 200                 205

Thr Lys Lys Leu Asn Glu Thr Cys Glu Ile Ile Asn Gly Leu Leu His
            210                 215                 220

Ala Pro Phe Asp Thr Lys Val Glu Lys Thr His Phe Ser Gln Phe Ile
225                 230                 235                 240

Asp Val Arg Asp Val Ala Lys Thr His Val Leu Gly Phe Gln Lys Asp
                245                 250                 255

Glu Leu Ile Asn Gln Arg Leu Leu Leu Cys Asn Gly Ala Phe Ser Gln
                260                 265                 270

Gln Asp Ile Val Asn Val Phe Asn Glu Asp Phe Pro Glu Leu Lys Gly
            275                 280                 285

Gln Phe Pro Pro Glu Lys Asp Thr Asp Leu Asn Lys Gly Val Thr
            290                 295                 300

Gly Cys Lys Ile Asp Asn Glu Lys Thr Lys Leu Leu Ala Phe Glu
305                 310                 315                 320

Phe Thr Pro Phe His Lys Thr Ile His Asp Thr Val Tyr Gln Ile Leu
                325                 330                 335

His Lys Glu Gly Arg Val
            340

<210> SEQ ID NO 2
<211> LENGTH: 342
<212> TYPE: PRT
<213> ORGANISM: Artificial Sequence
<220> FEATURE:
<223> OTHER INFORMATION: Protein translated from synthetic DNA

<400> SEQUENCE: 2

Met Ser Val Leu Ile Ser Gly Ala Ser Gly Tyr Ile Ala Lys His Ile
1               5                   10                  15

Val Arg Val Leu Leu Glu Gln Asn Tyr Lys Val Ile Gly Thr Val Arg
                20                  25                  30

Ser Gln Asp Lys Ala Asp Lys Leu Leu Lys Gln Tyr Asn Asn Pro Asn
            35                  40                  45

Leu Ser Tyr Glu Ile Val Pro Glu Ile Ala Asn Leu Asp Ala Phe Asp
            50                  55                  60

-continued

Asp Ile Phe Lys Lys His Gly Lys Glu Ile Lys Tyr Val Ile His Ala
 65                  70                  75                  80

Ala Ser Pro Ile Asn Phe Gly Ala Lys Asp Leu Glu Lys Asp Leu Val
                 85                  90                  95

Ile Pro Ala Ile Asn Gly Thr Lys Asn Met Phe Glu Ala Ile Lys Lys
            100                 105                 110

Tyr Ala Pro Asp Thr Val Glu Arg Val Val Met Thr Ala Ser Tyr Ala
            115                 120                 125

Ser Ile Met Thr Pro His Arg Gln Asn Asp Pro Thr Leu Thr Leu Asp
130                 135                 140

Glu Glu Thr Trp Asn Pro Val Thr Glu Asn Ala Tyr Glu Asn Val
145                 150                 155                 160

Phe Thr Ala Tyr Cys Ala Ser Lys Thr Phe Ala Glu Lys Glu Ala Trp
                165                 170                 175

Lys Phe Val Lys Glu Asn Ser Asp Ala Val Lys Phe Lys Leu Thr Thr
                180                 185                 190

Ile His Pro Ser Phe Val Phe Gly Pro Gln Asn Phe Asp Glu Asp Val
            195                 200                 205

Thr Lys Lys Leu Asn Glu Thr Cys Glu Ile Ile Asn Gly Leu Leu His
            210                 215                 220

Ala Pro Phe Asp Thr Lys Val Glu Lys Thr His Phe Ser Gln Phe Ile
225                 230                 235                 240

Asp Val Arg Asp Val Ala Lys Thr His Val Leu Gly Phe Gln Lys Asp
                245                 250                 255

Glu Leu Ile Asn Gln Arg Leu Leu Leu Cys Asn Gly Ala Phe Ser Gln
                260                 265                 270

Gln Asp Ile Val Asn Val Phe Asn Glu Asp Phe Pro Glu Leu Lys Gly
            275                 280                 285

Gln Phe Pro Pro Glu Asp Lys Asp Thr Asp Leu Asn Lys Gly Val Thr
            290                 295                 300

Gly Cys Lys Ile Asp Asn Glu Lys Thr Lys Lys Leu Leu Ala Phe Glu
305                 310                 315                 320

Phe Thr Pro Phe His Lys Thr Ile His Asp Thr Val Tyr Gln Ile Leu
                325                 330                 335

His Lys Glu Gly Arg Val
            340

<210> SEQ ID NO 3
<211> LENGTH: 342
<212> TYPE: PRT
<213> ORGANISM: Artificial Sequence
<220> FEATURE:
<223> OTHER INFORMATION: Protein translated from synthetic DNA

<400> SEQUENCE: 3

Met Ser Val Leu Ile Ser Gly Ala Ser Gly Tyr Ile Ala Lys His Ile
 1               5                  10                  15

Val Arg Val Leu Leu Glu Gln Asn Tyr Lys Val Ile Gly Thr Val Arg
                20                  25                  30

Ser Gln Asp Lys Ala Asp Lys Leu Leu Lys Gln Tyr Asn Asn Pro Asn
            35                  40                  45

Leu Ser Tyr Glu Ile Val Pro Glu Ile Ala Asn Leu Asp Ala Phe Asp
         50                  55                  60

Asp Ile Phe Lys Lys His Gly Lys Glu Ile Lys Tyr Val Ile His Ala
 65                  70                  75                  80

```
Ala Ser Pro Val Asn Phe Gly Ala Lys Asp Leu Glu Lys Asp Leu Val
                85                  90                  95

Ile Pro Ala Ile Asn Gly Thr Lys Asn Met Phe Glu Ala Ile Lys Lys
            100                 105                 110

Tyr Ala Pro Asp Thr Val Glu Arg Val Val Met Thr Ala Ser Cys Ala
        115                 120                 125

Ser Ile Met Thr Pro His Arg Gln Asn Asp Pro Thr Leu Thr Leu Asp
    130                 135                 140

Glu Glu Thr Trp Asn Pro Val Thr Glu Glu Asn Ala Tyr Glu Asn Val
145                 150                 155                 160

Phe Thr Ala Tyr Cys Ala Ser Lys Thr Phe Ala Glu Lys Glu Ala Trp
                165                 170                 175

Lys Phe Val Lys Glu Asn Ser Asp Ala Val Lys Phe Lys Leu Thr Thr
            180                 185                 190

Ile His Pro Ser Phe Val Phe Gly Pro Gln Asn Phe Asp Glu Asp Val
        195                 200                 205

Thr Lys Lys Leu Asn Glu Thr Cys Glu Ile Ile Asn Gly Leu Leu His
    210                 215                 220

Ala Pro Phe Asp Thr Lys Val Glu Lys Thr His Phe Ser Gln Phe Ile
225                 230                 235                 240

Asp Val Arg Asp Val Ala Lys Thr His Val Leu Gly Phe Gln Lys Asp
                245                 250                 255

Glu Leu Ile Asn Gln Arg Leu Leu Cys Asn Gly Ala Phe Ser Gln
            260                 265                 270

Gln Asp Ile Val Asn Val Phe Asn Glu Asp Phe Pro Glu Leu Lys Gly
        275                 280                 285

Gln Phe Pro Pro Glu Asp Lys Asp Thr Asp Leu Asn Lys Gly Val Thr
    290                 295                 300

Gly Cys Lys Ile Asp Asn Glu Lys Thr Lys Lys Leu Leu Ala Phe Glu
305                 310                 315                 320

Phe Thr Pro Phe His Lys Thr Ile His Asp Thr Val Tyr Gln Ile Leu
                325                 330                 335

His Lys Glu Gly Arg Val
            340

<210> SEQ ID NO 4
<211> LENGTH: 342
<212> TYPE: PRT
<213> ORGANISM: Artificial Sequence
<220> FEATURE:
<223> OTHER INFORMATION: Protein translated from synthetic DNA

<400> SEQUENCE: 4

Met Ser Val Leu Ile Ser Gly Ala Ser Gly Tyr Ile Ala Lys His Ile
1               5                   10                  15

Val Arg Val Leu Leu Glu Gln Asn Tyr Lys Val Ile Gly Thr Val Arg
            20                  25                  30

Ser Gln Asp Lys Ala Asp Lys Leu Leu Lys Gln Tyr Asn Asn Pro Asn
        35                  40                  45

Leu Ser Tyr Glu Ile Val Pro Glu Ile Ala Asn Leu Asp Ala Phe Asp
    50                  55                  60

Asp Ile Phe Lys Lys His Gly Lys Glu Ile Lys Tyr Val Ile His Ala
65                  70                  75                  80

Ala Ser Pro Val Asn Phe Gly Ala Lys Asp Leu Glu Lys Asp Leu Val
                85                  90                  95
```

Ile Pro Ala Ile Asn Gly Thr Lys Asn Met Phe Glu Ala Ile Lys Lys
            100                 105                 110

Tyr Ala Pro Asp Thr Val Glu Arg Val Val Met Thr Ala Ser Met Ala
            115                 120                 125

Ser Ile Met Thr Pro His Arg Gln Asn Asp Pro Thr Leu Thr Leu Asp
        130                 135                 140

Glu Glu Thr Trp Asn Pro Val Thr Glu Glu Asn Ala Tyr Glu Asn Val
145                 150                 155                 160

Phe Thr Ala Tyr Cys Ala Ser Lys Thr Phe Ala Glu Lys Glu Ala Trp
                165                 170                 175

Lys Phe Val Lys Glu Asn Ser Asp Ala Val Lys Phe Lys Leu Thr Thr
            180                 185                 190

Ile His Pro Ser Phe Val Phe Gly Pro Gln Asn Phe Asp Glu Asp Val
        195                 200                 205

Thr Lys Lys Leu Asn Glu Thr Cys Glu Ile Ile Asn Gly Leu Leu His
210                 215                 220

Ala Pro Phe Asp Thr Lys Val Glu Lys Thr His Val Phe Ser Gln Phe Ile
225                 230                 235                 240

Asp Val Arg Asp Val Ala Lys Thr His Val Leu Gly Phe Gln Lys Asp
                245                 250                 255

Glu Leu Ile Asn Gln Arg Leu Leu Leu Cys Asn Gly Ala Phe Ser Gln
            260                 265                 270

Gln Asp Ile Val Asn Val Phe Asn Glu Asp Phe Pro Glu Leu Lys Gly
        275                 280                 285

Gln Phe Pro Pro Glu Asp Lys Asp Thr Asp Leu Asn Lys Gly Val Thr
290                 295                 300

Gly Cys Lys Ile Asp Asn Glu Lys Thr Lys Lys Leu Leu Ala Phe Glu
305                 310                 315                 320

Phe Thr Pro Phe His Lys Thr Ile His Asp Thr Val Tyr Gln Ile Leu
                325                 330                 335

His Lys Glu Gly Arg Val
            340

```
<210> SEQ ID NO 5
<211> LENGTH: 342
<212> TYPE: PRT
<213> ORGANISM: Artificial Sequence
<220> FEATURE:
<223> OTHER INFORMATION: Protein translated from synthetic DNA

<400> SEQUENCE: 5
```

Met Ser Val Leu Ile Ser Gly Ala Ser Gly Tyr Ile Ala Lys His Ile
1               5                   10                  15

Val Arg Val Leu Leu Glu Gln Asn Tyr Lys Val Ile Gly Thr Val Arg
            20                  25                  30

Ser Gln Asp Lys Ala Asp Lys Leu Leu Lys Gln Tyr Asn Asn Pro Asn
        35                  40                  45

Leu Ser Tyr Glu Ile Val Pro Glu Ile Ala Asn Leu Asp Ala Phe Asp
    50                  55                  60

Asp Ile Phe Lys Lys His Gly Lys Glu Ile Lys Tyr Val Ile His Ala
65                  70                  75                  80

Ala Ser Pro Ile Asn Phe Gly Ala Lys Asp Leu Glu Lys Asp Leu Val
                85                  90                  95

Ile Pro Ala Ile Asn Gly Thr Lys Asn Met Phe Glu Ala Ile Lys Lys
            100                 105                 110

Tyr Ala Pro Asp Thr Val Glu Arg Val Val Met Thr Ala Ser Cys Ala
            115                 120                 125

Ser Ile Met Thr Pro His Arg Gln Asn Asp Pro Thr Leu Thr Leu Asp
130                 135                 140

Glu Glu Thr Trp Asn Pro Val Thr Glu Glu Asn Ala Tyr Glu Asn Val
145                 150                 155                 160

Phe Thr Ala Tyr Cys Ala Ser Lys Thr Phe Ala Glu Lys Glu Ala Trp
            165                 170                 175

Lys Phe Val Lys Glu Asn Ser Asp Ala Val Lys Phe Lys Leu Thr Thr
            180                 185                 190

Ile His Pro Ser Phe Val Phe Gly Pro Gln Asn Phe Asp Glu Asp Val
            195                 200                 205

Thr Lys Lys Leu Asn Glu Thr Cys Glu Ile Ile Asn Gly Leu Leu His
            210                 215                 220

Ala Pro Phe Asp Thr Lys Val Glu Lys Thr His Phe Ser Gln Phe Ile
225                 230                 235                 240

Asp Val Arg Asp Val Ala Lys Thr His Val Leu Gly Phe Gln Lys Asp
            245                 250                 255

Glu Leu Ile Asn Gln Arg Leu Leu Leu Cys Asn Gly Ala Phe Ser Gln
            260                 265                 270

Gln Asp Ile Val Asn Val Phe Asn Glu Asp Phe Pro Glu Leu Lys Gly
            275                 280                 285

Gln Phe Pro Pro Glu Asp Lys Asp Thr Asp Leu Asn Lys Gly Val Thr
            290                 295                 300

Gly Cys Lys Ile Asp Asn Glu Lys Thr Lys Lys Leu Leu Ala Phe Glu
305                 310                 315                 320

Phe Thr Pro Phe His Lys Thr Ile His Asp Thr Val Tyr Gln Ile Leu
            325                 330                 335

His Lys Glu Gly Arg Val
            340

<210> SEQ ID NO 6
<211> LENGTH: 342
<212> TYPE: PRT
<213> ORGANISM: Artificial Sequence
<220> FEATURE:
<223> OTHER INFORMATION: Protein translated from synthetic DNA

<400> SEQUENCE: 6

Met Ser Val Leu Ile Ser Gly Ala Ser Gly Tyr Ile Ala Lys His Ile
1               5                   10                  15

Val Arg Val Leu Leu Glu Gln Asn Tyr Lys Val Ile Gly Thr Val Arg
            20                  25                  30

Ser Gln Asp Lys Ala Asp Lys Leu Lys Gln Tyr Asn Asn Pro Asn
            35                  40                  45

Leu Ser Tyr Glu Ile Val Pro Glu Ile Ala Asn Leu Asp Ala Phe Asp
            50                  55                  60

Asp Ile Phe Lys Lys His Gly Lys Glu Ile Lys Tyr Val Ile His Ala
65                  70                  75                  80

Ala Ser Pro Ile Asn Phe Gly Ala Lys Asp Leu Glu Lys Asp Leu Val
            85                  90                  95

Ile Pro Ala Ile Asn Gly Thr Lys Asn Met Phe Glu Ala Ile Lys Lys
            100                 105                 110

Tyr Ala Pro Asp Thr Val Glu Arg Val Val Met Thr Ala Ser Met Ala
            115                 120                 125

```
Ser Ile Met Thr Pro His Arg Gln Asn Asp Pro Thr Leu Thr Leu Asp
        130                 135                 140

Glu Glu Thr Trp Asn Pro Val Thr Glu Glu Asn Ala Tyr Glu Asn Val
145                 150                 155                 160

Phe Thr Ala Tyr Cys Ala Ser Lys Thr Phe Ala Glu Lys Glu Ala Trp
                165                 170                 175

Lys Phe Val Lys Glu Asn Ser Asp Ala Val Lys Phe Lys Leu Thr Thr
                180                 185                 190

Ile His Pro Ser Phe Val Phe Gly Pro Gln Asn Phe Asp Glu Asp Val
            195                 200                 205

Thr Lys Lys Leu Asn Glu Thr Cys Glu Ile Ile Asn Gly Leu Leu His
210                 215                 220

Ala Pro Phe Asp Thr Lys Val Glu Lys Thr His Phe Ser Gln Phe Ile
225                 230                 235                 240

Asp Val Arg Asp Val Ala Lys Thr His Val Leu Gly Phe Gln Lys Asp
                245                 250                 255

Glu Leu Ile Asn Gln Arg Leu Leu Cys Asn Gly Ala Phe Ser Gln
                260                 265                 270

Gln Asp Ile Val Asn Val Phe Asn Glu Asp Phe Pro Glu Leu Lys Gly
            275                 280                 285

Gln Phe Pro Pro Glu Asp Lys Asp Thr Asp Leu Asn Lys Gly Val Thr
290                 295                 300

Gly Cys Lys Ile Asp Asn Glu Lys Thr Lys Lys Leu Leu Ala Phe Glu
305                 310                 315                 320

Phe Thr Pro Phe His Lys Thr Ile His Asp Thr Val Tyr Gln Ile Leu
                325                 330                 335

His Lys Glu Gly Arg Val
            340
```

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (10)..(11)
<223> OTHER INFORMATION: n is a, c, g, t or u

<400> SEQUENCE: 7
gcttcaccan nkaacttcgg c                                             21

<210> SEQ ID NO 8
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (11)..(12)
<223> OTHER INFORMATION: n is a, c, g, t or u

<400> SEQUENCE: 8
gccgaagttm nntggtgaag c                                             21

<210> SEQ ID NO 9
<211> LENGTH: 21
<212> TYPE: DNA

<213> ORGANISM: Artificial Sequence
<220> FEATURE:
<223> OTHER INFORMATION: Synthetic DNA
<220> FEATURE:
<221> NAME/KEY: misc_feature
<222> LOCATION: (10)..(11)
<223> OTHER INFORMATION: n is a, c, g, t or u

<400> SEQUENCE: 9
actgcttctn nkgcttcaat t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (11)..(12)
<223> OTHER INFORMATION: n is a, c, g, t or u

<400> SEQUENCE: 10
aattgaagcm nnagaagcag t                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
actgcttctt gtgcttcaat t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12
aattgaagca caagaagcag t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic DNA

<400> SEQUENCE: 13
actgcttcta tggcttcaat t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
aattgaagcc atagaagcag t                                              21

ALCOHOL DEHYDROGENASE MUTANT AND APPLICATION THEREOF IN COFACTOR REGENERATION

TECHNICAL FIELD

The present disclosure provides an alcohol dehydrogenase mutant and its application in cofactor regeneration, and belongs to the fields of enzyme engineering and bioengineering technology.

REFERENCE TO AN ELECTRONIC SEQUENCE LISTING

The contents of the electronic sequence listing filed on Aug. 3, 2020 (seq.txt; Size: 662,862 bytes; and Date of Creation: Mar. 21, 2020) is herein incorporated by reference in its entirety.

BACKGROUND

Cofactor NAD(P)H-dependent asymmetric bio-reduction reaction has many advantages such as high selectivity, mild conditions, and environmental friendliness, etc. It is one of the most promising method to be further developed for preparing chiral compounds. However, the cofactor NAD(P)H used therein is very expensive. In order to maintain the sustainability and efficiency of the asymmetric bio-reduction reaction, and to reduce the cost of the asymmetric bio-reduction reaction, the regeneration of the cofactor is required.

At present, existing cofactor regeneration methods include enzymatic regeneration, electrochemical regeneration, and photochemical regeneration. Among them, enzymatic regeneration has great potential in industrial application due to its advantages including high efficiency and selectivity, good compatibility between regeneration system and synthetic system, and easy operation.

In enzymatic cofactor regeneration, isopropanol and ethanol have low redox potential ($\Delta G'$-7.4 kcal·mol$^{-1}$) and are inexpensive. Therefore, the method of cofactor regeneration involving catalytic oxidation of isopropanol and ethanol by alcohol dehydrogenase (ADH) has the advantages of low price and high atom utilization efficiency.

However, in this method, acetaldehyde, a co-product of ethanol oxidation catalyzed by ADH, is toxic. Acetic acid generated by further catalytic oxidation will lower the pH value of the reaction system, which is not conducive to the bioreduction reaction. Acetone, a co-product of isopropanol oxidation catalyzed by ADH, is unstable and toxic. Moreover, because the process of isopropanol oxidization catalyzed by ADH to generate acetone is reversible, for the process of cofactor regeneration involving catalytic oxidation of isopropanol by ADH, excess isopropanol is usually required in order to maintain the bioreduction reaction process in the direction of target product synthesis. Therefore, it is urgent to find a new cofactor regeneration method to overcome the shortcomings of the above-mentioned technology.

In recent years, there have been some progresses in new methods for cofactor regeneration. For example, in 2008, Lavandera I and Kroutil W and others used alcohol dehydrogenase SyADH derived from *Sphingobium yanoikuyae* to catalyze the oxidation of acetone with an electron withdrawing group (such as chlorine, fluorine, methoxy, etc.) as co-substrates for the regeneration of the cofactor in the oxidation of secondary alcohols. These co-substrates have electron-withdrawing groups which can form hydrogen bonds with the hydroxyl groups in the co-products to stabilize the co-products ($\Delta G'$-11.1 kcal/mol), which makes the reaction tend to be irreversible (this reaction is called a quasi-irreversible reaction). Therefore, using this system, with 1-chloroacetone of only 1.5 equivalents the substrate, 30 g/L 2-octanol can be completely oxidized in 24 hours (Lavandera I., et al., *Org Lett.*, 2018, 10, 2155-2158).

Hollmann et al. found that 1,4-butanediol can be used as a smart co-substrate, which is first reduced to 4-hydroxybutyraldehyde during catalytic oxidation under the action of ADH, then spontaneously converted to 2-hydroxytetrahydrofuran, and finally, further irreversibly reduced to produce the final co-product γ-butyrolactone (GBL). The $\Delta G'$ of the whole process is −8.2 kcal·mol$^{-1}$, and two molecules of cofactor NADH are released. Therefore, 1,4-butanediol can be used as a smart co-substrate for cofactor regeneration. Further researches on this process showed that the co-product GBL produced by this process is kinetically and thermodynamically stable, which can change the chemical equilibrium of the Meerwein-Ponndorf-Verley reaction and hence reduce the excessive addition of co-substrates (Kara S., et al., *Green Chem.* 2013, 15, 330-335).

However, the above-mentioned studies still have the defects of low catalytic efficiency of enzymes and significant inhibition of the enzymatic catalysis by the substrate. Therefore, new methods of cofactor regeneration with high activity and no inhibition need to be further investigated.

SUMMARY

To solve above problems, the present disclosure provides an alcohol dehydrogenase mutant and its application in cofactor regeneration. The alcohol dehydrogenase mutant is obtained by mutating valine at position 84 and/or tyrosine at position 127 in alcohol dehydrogenase having an original amino acid sequence as set forth in SEQ ID No. 1. It has high catalytic activity for a variety of alcohol co-substrates (such as 1,4-butanediol, 1,5-pentanediol, and 1,6-hexanediol), and can catalyze these alcohol co-substrates to regenerate cofactor NADPH; compared with wild-type alcohol dehydrogenase KpADH, this alcohol dehydrogenase mutant has higher activity and catalytic efficiency. Toward co-substrate 1,4-butanediol, its $k_{cat}$ value can be up to 75.9 min$^{-1}$, which is 7.3 times that of wild-type KpADH. The $k_{cat}/K_m$ value can be up to 2009 min$^{-1}$·M$^{-1}$, which is 14.7 times that of wild-type KpADH. And its $K_m$ value can be as low as 11.3 mM, which is significantly lower than that of wild-type KpADH. Therefore, this KpADH mutant has a higher value in industrial application.

The technical solution of the present disclosure is as follows:

The present disclosure provides an alcohol dehydrogenase mutant, and the mutant is obtained by mutating valine at position 84 and/or tyrosine at position 127 in alcohol dehydrogenase having an original amino acid sequence as set forth in SEQ ID No. 1.

In an embodiment of the present disclosure, the mutants are M1, M2, M3, M4 or M5;

M1 is obtained by mutating valine at position 84 into isoleucine in alcohol dehydrogenase having an original amino acid sequence as set forth in SEQ ID No. 1;

M2 is obtained by mutating tyrosine at position 127 into cysteine in alcohol dehydrogenase having an original amino acid sequence as set forth in SEQ ID No. 1;

M3 is obtained by mutating tyrosine at position 127 into methionine in alcohol dehydrogenase having an original amino acid sequence as set forth in SEQ ID No. 1;

M4 is obtained by mutating valine at position 84 into isoleucine and tyrosine at position 127 into cysteine in alcohol dehydrogenase having an original amino acid sequence as set forth in SEQ ID No. 1;

the M5 is obtained by mutating valine at position 84 into isoleucine and tyrosine at position 127 into methionine in alcohol dehydrogenase having an original amino acid sequence as set forth in SEQ ID No. 1.

In an embodiment of the present disclosure, the amino acid sequence of the mutant is SEQ ID No. 2, SEQ ID No. 3, SEQ ID No. 4, SEQ ID No. 5 or SEQ ID No. 6.

The present disclosure provides a gene encoding the aforesaid mutant.

The present disclosure provides a recombinant plasmid carrying the aforesaid gene.

In an embodiment of the present disclosure, the recombinant plasmid vector is a pET vector.

In an embodiment of the present disclosure, the recombinant plasmid vector is pET28a (+).

The present disclosure provides a host cell carrying the aforesaid gene or the aforesaid recombinant plasmid.

In an embodiment of the present disclosure, the host cell is *Escherichia coli*.

In an embodiment of the present disclosure, the host cell is *E. coli* BL21 (DE3).

The present disclosure provides use of the aforesaid mutant or the aforesaid gene or the aforesaid recombinant plasmid or the aforesaid host cell in cofactor regeneration.

The present disclosure provides a method for producing an alcohol dehydrogenase mutant, and the method comprises the steps of inoculating the aforesaid host cell into an LB medium to culture at 30-40° C. with shaking at 100-200 r·min$^{-1}$ until the absorbance $OD_{600}$ in the medium reaches 0.5-1.0, and then adding isopropyl-β-D-thiogalactopyranoside (IPTG) to the medium for induction at 16-30° C. for 5-10 h to obtain an alcohol dehydrogenase mutant.

In an embodiment of the present disclosure, the LB medium is an LB medium containing 0-100 μg/mL kanamycin sulfate.

In an embodiment of the present disclosure, the addition amount of isopropyl-β-D-thiogalactopyranoside (IPTG) in the medium is 0.05-1.0 mmol/L.

The present disclosure provides a method for producing sodium D-phenylalanine. The method uses sodium phenylpyruvate, amino acid dehydrogenase DAADH$_{D94A}$, NADP$^+$ and one of $(NH_4)_2SO_4$, $NH_4Cl$ or $CH_3COONH_4$ as a reaction system, the aforesaid alcohol dehydrogenase mutant and one of 1,4-butanediol, 1,5-pentanediol, 1,6-hexanediol, isopropanol or 2,3-butanediol as a cofactor circulation system, and a buffer as a buffer system to conduct an asymmetric reduction reaction at 30-35° C. and a pH value of 7-9 for 1-24 h to obtain sodium D-phenylalanine.

In an embodiment of the present disclosure, the addition amount of the sodium phenylpyruvate in the reaction system is 10-200 mmol/L.

In an embodiment of the present disclosure, the addition amount of the amino acid dehydrogenase DAADH$_{D94A}$ in the reaction system is 0.5-5 kU/L.

In an embodiment of the present disclosure, the addition amount of the NADP$^+$ in the reaction system is 0.1-1.0 mmol/L.

In an embodiment of the present disclosure, the addition amount of the $(NH_4)_2SO_4$ in the reaction system is 20-200 mmol/L.

In an embodiment of the present disclosure, the addition amount of the 1,4-butanediol in the reaction system is 5-100 mmol/L.

In an embodiment of the present disclosure, the addition amount of the alcohol dehydrogenase mutant in the reaction system is 0.3-3 kU/L.

In an embodiment of the present disclosure, the buffer is a phosphate buffer, a glycine-sodium hydroxide buffer, or a Tris-HCl buffer.

In an embodiment of the present disclosure, the buffer is a phosphate buffer.

In an embodiment of the present disclosure, the concentration of the phosphate buffer is 10-200 mmol/L.

Beneficial Effects:

(1) The alcohol dehydrogenase mutant of the present disclosure has high vitality for various alcohol co-substrates (such as 1,4-butanediol, 1,5-pentanediol, and 1,6-hexanediol), and can catalyze these alcoholic co-substrates to regenerate cofactor NADPH;

(2) Compared with wild-type alcohol dehydrogenase KpADH, the alcohol dehydrogenase mutant of the present disclosure has higher activity and catalytic efficiency, and for the co-substrate 1,4-butanediol, its $k_{cat}$ value can be up to 75.9 min$^{-1}$, which is 7.3 times that of wild-type KpADH, and its $k_{cat}/K_m$ value can be up to 2009 min$^{-1}$·M$^{-1}$, which is 14.7 times that of wild-type KpADH, and its $K_m$ value can be as low as 11.3 mM, which is significantly lower than that of wild-type alcohol dehydrogenase KpADH. Therefore, the alcohol dehydrogenase mutant of the present disclosure has a higher potential value in industrial application.

(3) The alcohol dehydrogenase mutant of the present disclosure is coupled to the amino acid dehydrogenase DAADH$_{D94A}$ to catalyze the production of sodium D-phenylalanine from sodium phenylpyruvate with a product yield of >99% and an ee value of >99.9%. Therefore, the alcohol dehydrogenase mutant of the present disclosure is highly efficient in the cofactor regeneration, can be used in the amino acid dehydrogenase reaction, and has a high value in industrial promotion.

DETAILED DESCRIPTION

The present disclosure is further described below in conjunction with specific examples. The primers, vectors, and host cells involved in the following examples are only used for the purpose of illustrating the present disclosure without any limitations thereto.

Detection methods involved in the following embodiment s are as follows:

Method for Detecting Alcohol Dehydrogenase Activity:

The total reaction system is 200 μL, comprising: 1.0 mM NADP$^+$, 200 mM 1,4-butanediol as the substrate, and glycine sodium hydroxide buffer (Gly-NaOH, 100 mM, pH 9.5), which are thoroughly mixed, incubated at 30° C. for 2 min, and then an appropriate amount of an enzyme solution is added thereto. Changes in absorbance at 340 nm are measured.

The enzyme activity is calculated using the following formula:

$$\text{Enzyme activity }(U)=EW\times V\times 10^3/(6220\times I);$$

In the formula, EW is the change in absorbance at 340 nm in 1 min; V is the volume of the reaction solution in mL; 6220 is the molar extinction coefficient of NAD(P)H in L/(mol·cm); I is optical distance in cm.

One unit of activity (U) corresponds to the amount of enzyme required for the catalytic oxidation of 1 μmol NADP$^+$ per minute under the above conditions.

Method for Determination of $k_{cat}$, $K_m$ and $k_{cat}/K_m$ Values:

Kinetic measurement is conducted according to the enzyme activity assay, with 10 μL of alcohol substrates of different concentrations, 1 mM NADP$^+$, 10 μL of enzymes of appropriate concentrations, 170 μL of glycine-sodium hydroxide buffer at pH 9.5, with each sample in triplicate. The change in OD$_{340}$ at 30° C. is measured to calculate the specific activity at different concentrations, and further calculate the Michaelis constant ($K_m$), the maximum reaction velocity ($V_{max}$) and the catalytic rate ($k_{cat}$). The calculation formulas are as follows:

$$\frac{1}{V}=\frac{K_m}{V_{max}}\times\frac{1}{[S]}+\frac{1}{V_{max}};$$

The $V_{max}$ and $K_m$ values can be calculated from the intercepts of the double reciprocal plot on the X and Y axes;

$$k_{cat}=\frac{V_{max}}{[E]};$$

The $k_{cat}$ value can be further calculated according to the formula.

Figure 5:
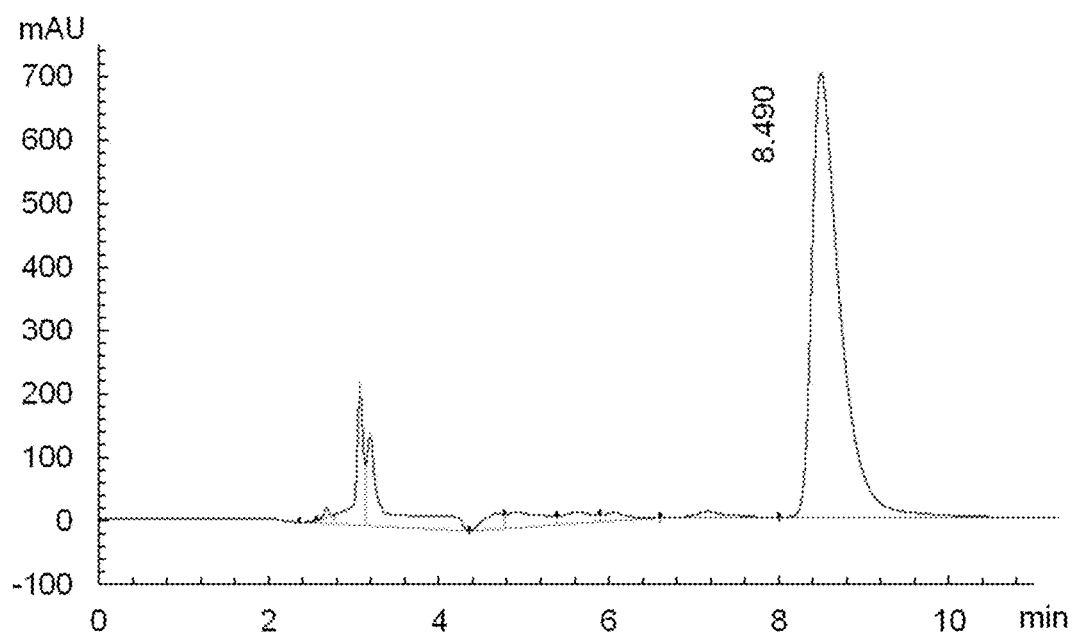
FIG. 5: Chiral chromatogram of product D-phenylalanine produced from sodium phenylpyruvate catalyzed by the enzyme-coupled cofactor regeneration reaction.

Method for Detecting the Yield of Product D-Sodium Phenylalanine:

The reacted sample is passed through a membrane and then tested by liquid chromatography where an Astec CHIROBIOTIC™ T chiral column (150 mm×4.6 mm×5 μm, Sigma Technologies Co. Ltd) is used, the mobile phase is methanol:ultrapure water=70:30, the flow rate is 0.5 mL·min$^{-1}$, the column oven is set at a temperature of 30° C., the UV absorption wavelength is 210 nm, and the retention time of the product sodium D-phenylalanine is 8.49 min. The liquid chromatogram is shown in FIG. 5.

Method for Detecting Optical Purity of Product D-Phenylalanine:

Method for detecting optical purity ee:

$$ee=\frac{A_S-A_R}{A_S+A_R}\times 100\%;$$

In the formula, $A_S$ is the molar concentration of sodium D-phenylalanine obtained by liquid chromatography; $A_R$ is the molar concentration of sodium L-phenylalanine obtained by liquid chromatography.

Figure 6:
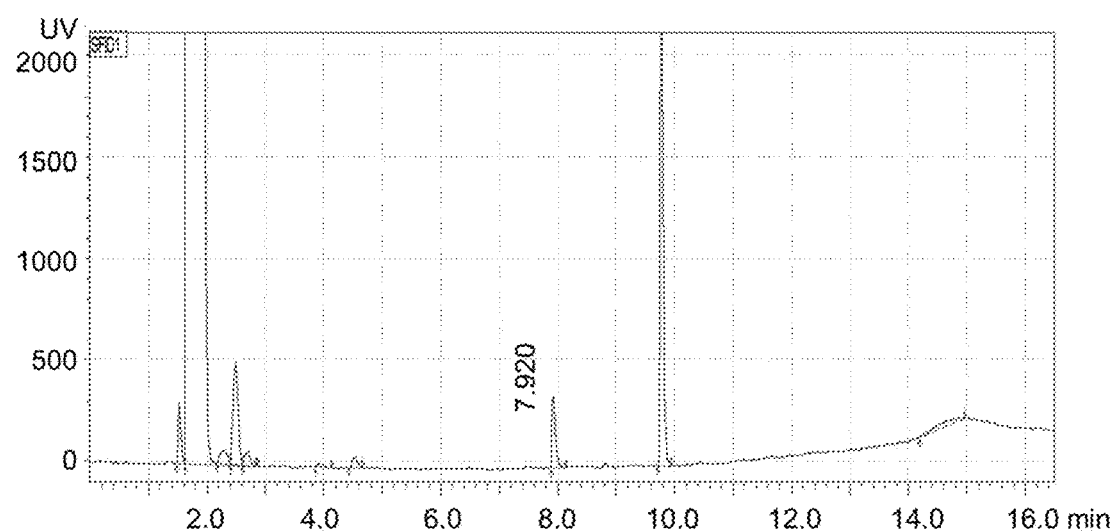
FIG. 6: Gas chromatogram of coproduct γ-butyrolactone in the enzyme-coupled cofactor regeneration reaction.

Method for Detecting Yield of Co-Product γ-Butyrolactone:

The co-product γ-butyrolactone is detected by gas chromatography with a CP-Chirasil-Dex CB column (25 m×0.25 mm×0.25 μm, Agilent Technologies Co. Ltd). The column temperature is maintained at 70° C. for 5 min and then increased at a rate of 20° C./min to 200° C. which is maintained for 5 min. The temperature of both the vaporization chamber and the detector is set to 250° C. The retention time of γ-butyrolactone is 7.92 min. The gas chromatogram is shown in FIG. 6.

Embodiment 1: Construction of Recombinant Vectors and Recombinant Bacteria Containing Genes Encoding Alcohol Dehydrogenase Mutants M1 to M5

Specifically, the steps are as follows:

Using the recombinant plasmid pET28a-KpADH deposited in the laboratory as a template (described in the patent application with publication number CN105936909A), the amino acid residues at position 84 and position 127 of ADH having an amino acid sequence set forth in SEQ ID NO.1 underwent site-saturation mutagenesis by using the full-plasmid PCR method to obtain recombinant vectors comprising M1, M2, and M3. Then, using the M1 recombinant plasmid as a template, the residue at position 127 of M1 underwent site-saturation mutation by using the full-plasmid PCR method to obtain recombinant vectors comprising M4 and M5;

The primers involved are as follows (all described in the 5'-3' direction, and the underline represents the mutation site):

M1:
V84-F having an amino acid sequence set forth in SEQ. ID No. 7:
GCTTCACCA<u>nnk</u>AACTTCGGC;

V84-R having an amino acid sequence set forth in SEQ. ID No. 8:
GCCGAAGTT<u>mnn</u>TGGTGAAGC;

M2, M3:
Y127-F having an amino acid sequence set forth in SEQ. ID No. 9:
ACTGCTTCT<u>nnk</u>GCTTCAATT;

Y127-R having an amino acid sequence set forth in SEQ. ID No. 10:
AATTGAAGC<u>mnn</u>AGAAGCAGT;

M4:
V84I/Y127C-F having an amino acid sequence set forth in SEQ. ID No. 11:
ACTGCTTCT<u>tgt</u>GCTTCAATT;

V84I/Y127C-R having an amino acid sequence set forth in SEQ. ID No. 12:
AATTGAAGC<u>aca</u>AGAAGCAGT;

-continued

M5:
V84I/Y127M-F having an amino acid
sequence set forth in SEQ. ID No. 13:
ACTGCTTCTatgGCTTCAATT;

V84I/Y127M-R having an amino acid
sequence set forth in SEQ. ID No. 14:
AATTGAAGCcatAGAAGCAGT;

Among others, the PCR reaction system (50 μL) consists of: 1.0 μL of KOD enzyme (2.5 U/mL), 1.0 μL of template (5-50 ng), 4.0 μL of dNTP, 5.0 μL of 10× reaction buffer, upstream and downstream primers, 1.0 μL each, and ddH$_2$O making up to 50 μL;

The PCR amplification procedure consists of: (1) denaturation at 94° C. for 3 min, (2) denaturation at 94° C. for 30 sec, (3) annealing at 54° C. for 30 sec, (4) extension at 72° C. for 150 sec, repeating steps (2) to (4) for 10-15 cycles, and finally extension at 72° C. for 10 min; the PCR amplification product is stored at 4° C.

After the PCR was completed, DpnI restriction endonuclease was added to the reaction mixture and incubated at 37° C. for 1 h. Ten μL of the digested PCR reaction solution was transferred into 50 μL of E. coli BL21 (DE3) competent cells by the CaCl$_2$ thermal transformation method, and spread onto an LB agar plate containing 50 μg/ml kanamycin sulfate and cultivated at 37° C. for 12 h to obtain recombinant bacteria harboring the recombinant plasmids.

Embodiment 2: Screening of Recombinant Bacteria Harboring Recombinant Vectors

Specifically, the steps are as follows:
Recombinant bacteria with alcohol dehydrogenase mutants M1 to M3 were obtained according to Embodiment 1, and were cultured to obtain bacterial colonies;

300 μL of an LB liquid medium containing kanamycin (Kan) was added to each well of a 96-deep-well plate, and then the single colonies on the plate in Embodiment 1 were picked out one by one with toothpicks and placed into the deep-well plate, leaving two wells with the wild type KpADH as controls and two wells without inoculation as blank controls. The plate was placed on a shaker to culture overnight at 37° C. and 120 r·min$^{-1}$;

The next day, the cultured recombinant bacteria were transferred to another 96-deep-well plate with 600 μL of a liquid medium supplemented with kan. 70 μL of 30% glycerol was added to each well of the original plate which was placed at −80° C. for preserving the bacteria. The other deep-well plate was placed in a shaker to culture at 37° C. with shaking at 120 r·min$^{-1}$ for 2 h. Thereafter, the inducer IPTG was added (to a final concentration of 0.2 mmol·L$^{-1}$). The plate was cultured at a temperature of 30° C. with shaking for 5 h, and then centrifuged at 4° C. and 4000 r·min$^{-1}$ for 10 min. The supernatant was discarded, and the plate was frozen at −80° C. for more than 1 h, and then 200 μL of a lysis buffer (pH 7.5, 10 mmol·L$^{-1}$ Tris-HCl, 750 mg·L$^{-1}$ lysozyme, and 10 mg·L$^{-1}$ DNase) was added to each well. The plate was cultured at 37° C. with shaking at 120 r·min$^{-1}$ for 1 h.

The plate was centrifuged and the supernatant was taken to determine the specific activity of the KpADH mutants for 1,4-butanediol. The alcohol dehydrogenase mutants with improved specific activity were selected and verified by sequencing, thereby obtaining recombinant bacteria containing recombinant plasmids that successfully overexpressed alcohol dehydrogenase mutants M1-M3 (the results of full plasmid PCR nucleic acid electrophoresis of M1-M3 are shown in FIG. 1).

Figure 1:
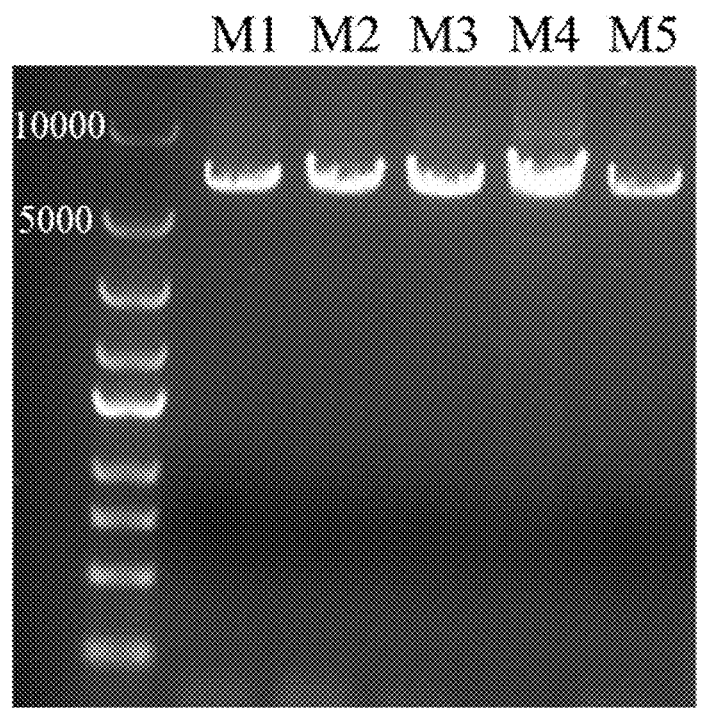
FIG. 1: Electrophoresis of whole plasmid PCR of wild-type alcohol dehydrogenase KpADH and its mutants M1-M5.

M4 and M5 can be directly obtained by site-directed mutagenesis of the 127th position of M1 by using the full-plasmid PCR method using the recombinant plasmid comprising M1 as a template (see FIG. 1).

Embodiment 3: Expression and Purification of Alcohol Dehydrogenase Mutants M1 to M5

1. Expression
Specifically, the steps are as follows:
The recombinant bacteria harboring the recombinant plasmids obtained in Embodiment 1 were inoculated into a LB medium containing kanamycin sulfate (50 μg/mL) at a inoculation amount of 2% to culture with shaking at 37° C. and 200 r·min$^{-1}$. When the absorbance OD$_{600}$ of the culture solution reached 0.8, 0.2 mM isopropyl-β-D-thiogalactopyranoside (IPTG) was added for induction at 25° C. for 8 h, which was followed by centrifugation at 8000 r·min$^{-1}$ for 10 min, thereby obtaining recombinant bacterial strains expressing alcohol dehydrogenase mutants M1-M5. The collected bacterial strains were suspended in a potassium phosphate buffer solution (100 mM, pH 7.0) and ultrasonicated to obtain alcohol dehydrogenase mutants M1-M5.

2. Purification
The purification was conducted using a nickel affinity column HisTrap FF crude by affinity chromatography using the histidine tag on the recombinant protein. The specific steps are as follows:

First, the nickel column was equilibrated with solution A, and loaded with the crude enzyme solution. Further, solution A was used to elute the breakthrough peak. After equilibration, gradient elution was performed using solution B (20 mM sodium phosphate, 500 mM NaCl, 500 mM imidazole, pH 7.4) to elute the recombinant protein bound to the nickel column to obtain purified alcohol dehydrogenase mutants M1 to M5. After purification, the alcohol dehydrogenase protein was concentrated and displaced using a 10 kDa ultrafiltration tube into PBS (100 mM, pH 7.0) buffer for later use.

The purified alcohol dehydrogenase mutants M1-M5 were tested for activity and analyzed by SDS-PAGE.

Figure 2:
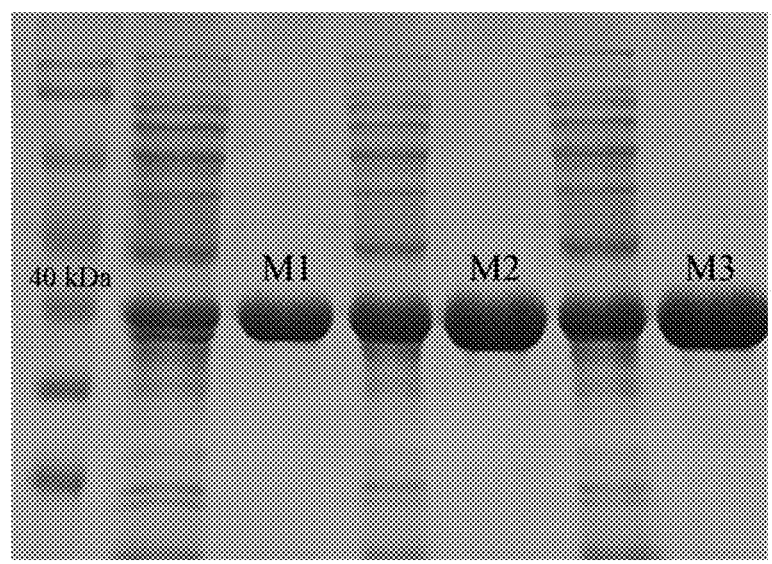
FIG. 2: Electrophoresis of gradient elution of alcohol dehydrogenase mutants M1-M3.
Figure 3:
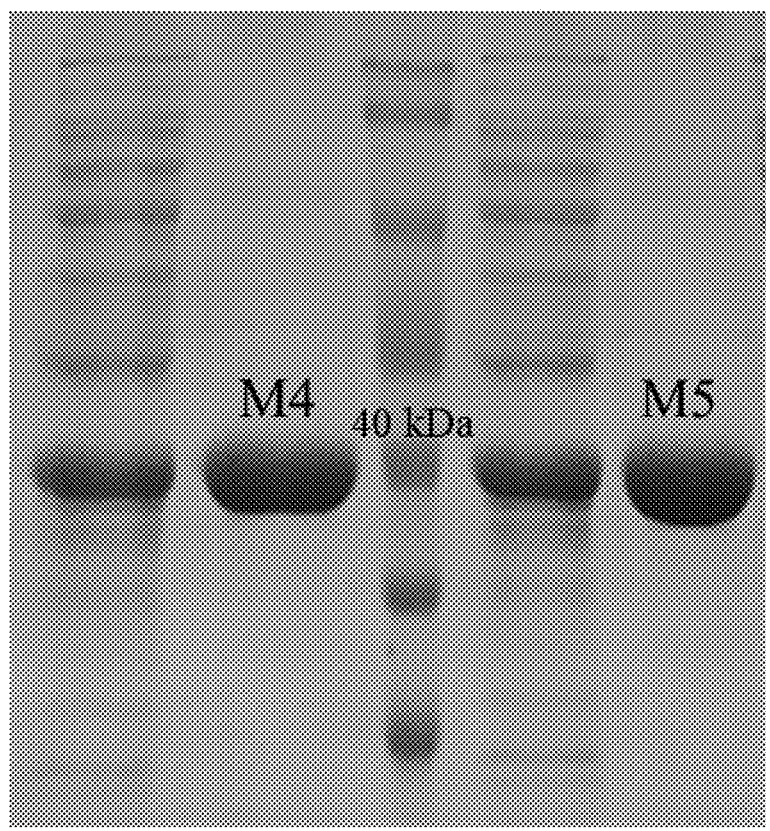
FIG. 3: Electrophoresis of gradient elution of alcohol dehydrogenase mutant M4-M5.

Detection results: as shown in FIGS. 2 and 3 and as analyzed by SDS-PAGE, after purification on a nickel column, the alcohol dehydrogenase mutants M1 to M5 showed a single band at about 40 kDa, and there were fewer other proteins, indicating good purification effects.

Embodiment 4: Kinetic Analysis of Alcohol Dehydrogenase Mutants M1-M5 for the Smart Co-Substrate 1,4-Butanediol The activity of KpADH under different substrate concentrations and cofactor concentrations was measured, and a double reciprocal plot was made according to the reciprocals of the activity and substrate concentration. The kinetic parameters were calculated. The results are shown in Table 1.

As can be seen from Table 1, the mutant M1 plays an important role in the oxidation of 1,4-butanediol. Its $k_{cat}$ value was 75.9 min$^{-1}$, which was 7.3 times that of wild-type KpADH, and its $k_{cat}/K_m$ value was 620 min$^{-1}$·M$^{-1}$, which was 4.53 times that of wild-type KpADH; the $K_m$ values of M2 and M3 for 1,4-butanediol were 38.1 mM and 12.1 mM, respectively, and their catalytic rates $k_{cat}$ were 27.8 mM and 16.8 mM, respectively. As can be seen, the Y127 site significantly reduced the $K_m$ value, which plays a positive role in binding of the substrate 1,4-butanediol; the mutant M5 had the highest $k_{cat}/K_m$ value of 2009 $min^{-1} \cdot M^{-1}$, which was 14.7 times of that of the wild-type KpADH.

TABLE 1

Kinetic parameters of KpADH mutants toward 1,4-butanediol

| Variant | $K_M$[mM] | $k_{cat}$[min$^{-1}$] | $k_{cat}/K_M$[min$^{-1} \cdot$M$^{-1}$] |
|---|---|---|---|
| KpADH | 75.6 ± 0.4 | 10.4 ± 0.4 | 137 |
| M1 | 122 ± 2.1 | 75.9 ± 1.3 | 620 |
| M2 | 38.1 ± 1.9 | 27.8 ± 0.5 | 729 |
| M3 | 12.1 ± 0.9 | 16.8 ± 1.1 | 1390 |

TABLE 1-continued

Kinetic parameters of KpADH mutants toward 1,4-butanediol

| Variant | $K_M$[mM] | $k_{cat}$[min$^{-1}$] | $k_{cat}/K_M$[min$^{-1} \cdot$M$^{-1}$] |
|---|---|---|---|
| M4 | 30.4 ± 1.3 | 39.1 ± 0.4 | 1286 |
| M5 | 11.3 ± 0.8 | 22.7 ± 1.1 | 2009 |

Embodiment 5: Kinetic Analysis of the KpADH Mutants M1-M5 Towards Alcohol Co-Substrates 1,5-Pentanediol and 1,6-Hexanediol The activity of KpADH under different substrate concentrations and cofactor concentrations was measured, and a double reciprocal plots were made according to the reciprocals of the activity and substrate concentration. The kinetic parameters were calculated. The results are shown in Table 2.

It can be seen from Table 2 that better catalytic efficiency was achieved for these two diol substrates with longer carbon chains as compared with 1,4-butanediol. Among others, the $K_m$ values of the mutant M1 for 1,5-pentanediol and 1,6-hexanediol were 42.5 mM and 12.3 mM, respectively, and their $k_{cat}$ values were 51.1 min$^{-1}$ and 64.7 min$^{-1}$, respectively, indicating that both the binding capacity and catalytic rate of M1 for these two diol substrates are improved;

The $K_m$ value of mutant M3 for 1,5-pentanediol was low as 14.3 mM, compared to 74.4 mM in the case of wild-type KpADH, and its $K_m$ value for 1,6-hexanediol was as low as 6.48 mM, compared to 18.5 mM in the case of wild-type KpADH. This is mainly due to the improvement in substrate affinity;

The catalytic efficiency $k_{cat}/K_m$ of M3 for 1,5-pentanediol and 1,6-hexanediol was 4.36 and 2.69 times that of wild-type KpADH, respectively;

The $K_m$ values of double mutant M5 for 1,5-pentanediol and 1,6-hexanediol were 8.21 mM and 6.52 mM respectively, which were far lower than those of wild-type KpADH (74.4 mM and 18.5 mM), and their catalytic efficiency $k_{cat}/K_m$ was 2353 min$^{-1} \cdot$M$^{-1}$ and 12032 min$^{-1} \cdot$M$^{-1}$, which is 3.14 and 5.3 times the wild-type KpADH respectively. This indicates that the double mutant M5 is a promising mutant for catalytic oxidation of diol substrates to regenerate NADPH.

TABLE 2

Kinetic parameters of alcohol dehydrogenase mutants toward 1,5-pentanediol and 1,6-hexanediol

| Variant | $K_M$[mM] | $k_{cat}$[min$^{-1}$] | $k_{cat}/K_M$ [min$^{-1} \cdot$M$^{-1}$] | $K_M$[mM] | $k_{cat}$[min$^{-1}$] | $k_{cat}/K_M$ [min$^{-1} \cdot$M$^{-1}$] |
|---|---|---|---|---|---|---|
| KpADH | 74.4 ± 2.2 | 55.7 ± 1.0 | 749 | 18.5 ± 1.5 | 41.9 ± 0.9 | 2269 |
| M1 | 42.5 ± 1.5 | 51.1 ± 0.8 | 1202 | 12.3 ± 0.7 | 64.7 ± 1.7 | 5252 |
| M2 | 63.5 ± 0.1 | 25.1 ± 0.9 | 396 | 31.8 ± 1.7 | 36.2 ± 2.2 | 1138 |
| M3 | 14.3 ± 0.9 | 46.6 ± 1.7 | 3269 | 6.48 ± 0.45 | 39.5 ± 1.9 | 6093 |
| M4 | 16.3 ± 0.8 | 24.8 ± 1.1 | 1521 | 12.9 ± 1.3 | 98.3 ± 2.5 | 7630 |
| M5 | 8.21 ± 0.22 | 19.3 ± 0.9 | 2353 | 6.52 ± 1.0 | 75.2 ± 2.1 | 12032 |

Embodiment 6: Production of Sodium D-Phenylalanine from Sodium Phenylpyruvate as Catalyzed by Alcohol Dehydrogenase Mutants M1, M2, M5 Coupled to Amino Acid Dehydrogenase DAADH$_{D94A}$ The amino acid dehydrogenase DAADH$_{D94A}$ derived from Ureibacillus thermosphaericus can catalyze the production of D-phenylalanine, which is an important chiral component of drug nateglinide for the treatment of type 2 diabetes, from the substrate sodium phenylpyruvate. However, the catalytic reaction requires the addition of expensive cofactor NADPH.

The alcohol dehydrogenase mutants M1, M2, and M5 obtained in Embodiment 3 were used to regenerate NADPH to construct an enzyme-coupled cofactor regeneration reaction to produce sodium D-phenylalanine below. The specific steps are as follows:

Establishment of a 50 mM biocatalytic system of substrate sodium phenylpyruvate: alcohol dehydrogenase mutant M1, M2, M5 or wild-type KpADH pure enzyme (protein concentration 1.5 kU/L) or glucose dehydrogenase GDH (1.5 kU/L), DAADH$_{D94A}$ (5 kU/L), substrate sodium phenylpyruvate (50 mM), co-substrate 1,4-butanediol (50 mM), and (NH$_4$)$_2$SO$_4$ (100 mM);

The biocatalytic system reacted at 30° C. and 180 r·min$^{-1}$, and was sampled over time to detect the yield of sodium D-phenylalanine in the reaction. The results are shown in Table 3.

It can be seen from Table 3 that 4 h after the reaction began, for wild-type KpADH, the yield of the product was only 46.4%, while the yields of sodium D-phenylalanine in NADPH regeneration reaction of mutants M1 and M2 were increased to 88.0% and 89.0%, respectively, and for mutant M5, the yield of sodium D-phenylalanine was 99.9% in 4 h, with an e.e. value of >99.9%.

TABLE 3

Preparation of sodium D-phenylalanine by enzyme-coupled cofactor regeneration reaction

| Reaction time (h) | Conversion rate (%) | | | | |
|---|---|---|---|---|---|
| | WT | GDH | M1 | M2 | M5 |
| 0.5 | 5.1 | 67.0 | 36.4 | 43.5 | 88.3 |
| 1 | 11.5 | 72.1 | 71.6 | 77.6 | 96.1 |
| 1.5 | 17.9 | 72.4 | 80.8 | 78.4 | 97.9 |
| 2 | 24.8 | 74.3 | 85.4 | 82.4 | 98.2 |
| 3 | 39.3 | 74.4 | 87.0 | 88.3 | 99.7 |
| 4 | 46.4 | 74.4 | 88.0 | 89.0 | 99.9 |

Figure 4:
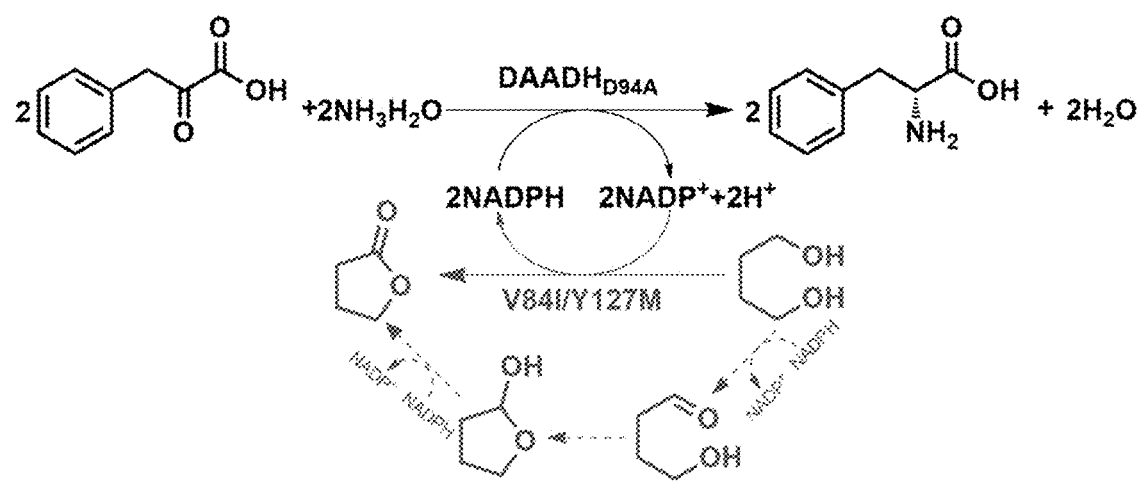
FIG. 4: Schematic diagram of the enzyme-coupled cofactor regeneration reaction system.

Embodiment 7: Production of Sodium D-Phenylalanine from Sodium Phenylpyruvate as Catalyzed by Alcohol Dehydrogenase Mutant M5-Coupled to Amino Acid Dehydrogenase DAADH$_{D94A}$ The optimal alcohol dehydrogenase mutant M5 as determined in Embodiment 6 was used to regenerate NADPH to construct an enzyme-coupled cofactor regeneration system, and the amount of co-substrate 1,4-butanediol was reduced to 0.5 equivalent. Specifically, the steps are as follows (the reaction of the regeneration system is shown in FIG. 4):

Establishment of a 100 mM biocatalytic system A of substrate sodium phenylpyruvate: alcohol dehydrogenase mutant M5 (1.5 kU/L), DAADH$_{D94A}$ (5 kU/L), substrate sodium phenylpyruvate (100 mM), co-substrate 1,4-butanediol (50 mM), and (NH$_4$)$_2$SO$_4$ (200 mM);

Establishment of a 200 mM biocatalytic system B of substrate sodium phenylpyruvate: alcohol dehydrogenase mutant M5 (protein concentration 10 mg/mL), DAADH$_{D94A}$ (5 kU/L), substrate sodium phenylpyruvate (200 mM), co-substrate 1,4-butanediol (100 mM), and (NH$_4$)$_2$SO$_4$ (200 mM);

Both the biocatalytic systems A and B reacted at 30° C. and 180 r·min$^{-1}$, and were sampled over time to determine the yield of sodium D-phenylalanine and co-product γ-butyrolactone. The results are shown in Table 4.

It can be seen from Table 4 that in the reaction of 100 mM substrate, the yield of sodium D-phenylalanine reached 99.8% in 2 h, and the yield of γ-butyrolactone reached 90.6% in 1 h; when the addition amount of substrate sodium phenylpyruvate was further increased to 200 mM and the addition amount of co-substrate 1,4-butanediol was increased to 100 mM accordingly, the yield of the product D-phenylalanine sodium reached 99.2% in 6 h, and the yield of the co-product γ-butyrolactone reached 90.3% (see FIG. 5 for the chiral chromatogram of the product sodium D-phenylalanine and FIG. 6 for the gas chromatogram of the co-product γ-butyrolactone).

TABLE 4

Detection of D-phenylalanine in coupling reaction using M5 for regeneration of NADPH

| Reaction time (h) | D-phenylalanine yield (%) | |
|---|---|---|
| | 100 mM | 200 mM |
| 0 | 0 | 0 |
| 0.5 | 67.6 | 26.1 |
| 1 | 98.5 | 41.1 |
| 1.5 | 98.8 | 60.6 |
| 2 | 99.8 | 77.6 |
| 3 | 99.9 | 95.0 |
| 4 | 99.9 | 98.5 |
| 6 | 99.9 | 99.2 |

TABLE 5

Detection of γ-butyrolactone in coupling reaction using M5 for regeneration of NADPH

| Reaction time (h) | γ-butyrolactone yield (%) | |
|---|---|---|
| | 100 mM | 200 mM |
| 0 | 0 | 0 |
| 0.5 | 62.6 | 26.8 |
| 1 | 90.6 | 45.6 |
| 1.5 | 88.7 | 65.9 |
| 2 | 85.9 | 80.0 |
| 3 | 84.9 | 85.6 |
| 4 | 85.7 | 87.1 |
| 6 | 84.6 | 90.3 |

What is claimed is:

1. An alcohol dehydrogenase mutant, wherein the alcohol dehydrogenase mutant comprises the amino acid sequence of SEQ ID NO: 1 except for substitutions) selected from the group consisting of:
- a substitution of valine at position 84 of SEQ ID NO: 1 with isoleucine,
- a substitution of tyrosine at position 127 of SEQ ID NO: 1 with cysteine,
- a substitution of tyrosine at position 127 of SEQ ID NO: 1 with methionine,
- a substitution of valine at position 84 of SEQ ID NO: 1 with isoleucine and a substitution of tyrosine at position 127 of SEQ ID NO: 1 with cysteine, and
- a substitution of valine at position 84 of SEQ ID NO: 1 with isoleucine and a substitution of tyrosine at position 127 of SEQ ID NO: 1 with methionine, and wherein the alcohol dehydrogenase mutant possesses alcohol dehydrogenase activity.

2. An alcohol dehydrogenase mutant, wherein the amino acid sequence of the alcohol dehydrogenase mutant is SEQ ID NO: 2, SEQ ID NO: 3, SEQ ID NO: 4, SEQ ID NO: 5, or SEQ ID NO: 6.

3. A method for producing sodium D-phenylalanine, comprising combining the alcohol dehydrogenase mutant of claim 1, sodium phenylpyruvate, amino acid dehydrogenase $DAADH_{D94A}$, NADP+, one of $(NH_4)_2SO_4$, $NH_4Cl$ or $CH_3COONH_4$, and one of 1,4-butanediol, 1,5-pentanediol, 1,6-hexanediol, isopropanol or 2,3-butanediol in a buffer to conduct an asymmetric reduction reaction at 30-35° C. and a pH value of 7-9 for 1-24 h to obtain sodium D-phenylalanine.

4. The method of claim 3, wherein the amount of the sodium phenylpyruvate is 10-200 mmol/L.

5. The method of claim 3, wherein the amount of the amino acid dehydrogenase $DAADH_{D94A}$ is 0.5-5 kU/L.

6. The method of claim 3, wherein the amount of the NADP+ is 0.1-1.0 mmol/L.

7. The method of claim 3, wherein the amount of the $(NH_4)_2SO_4$ is 20-200 mmol/L.

8. The method of claim 3, wherein the amount of the 1,4-butanediol is 5-100 mmol/L.

9. The method of claim 3, wherein the amount of the alcohol dehydrogenase mutant is 0.3-3 kU/L.

* * * * *